United States Patent [19]
Gargas

[11] Patent Number: 5,668,015
[45] Date of Patent: Sep. 16, 1997

[54] METHOD FOR MEASURING ORGANICS LEVELS IN AN AQUARIUM

[75] Inventor: Joseph E. Gargas, Apollo Beach, Fla.

[73] Assignee: Wardley Corporation, Secaucus, N.J.

[21] Appl. No.: 569,892

[22] Filed: Dec. 8, 1995

[51] Int. Cl.[6] .................................................. G01N 33/18
[52] U.S. Cl. ....................... 436/146; 422/61; 422/79; 436/127
[58] Field of Search ............................. 436/145, 127, 436/146; 422/79, 80, 61

[56] References Cited

U.S. PATENT DOCUMENTS 4,619,902  10/1986  Bernard .................................. 436/145

OTHER PUBLICATIONS

BIOSIS 94: 184925.
BIOSIS 87: 406684.
BIOSIS 81: 150289.

*Primary Examiner*—Lyle A. Alexander
*Attorney, Agent, or Firm*—Stroock & Stroock & Lavan LLP

[57] ABSTRACT

A kit and method are provided for determining the suitability of the level of organic material in an aquarium. A test sample of water is removed from an aquarium into a test sample container. The pH of the test sample can be lowered and then a quantity of potassium permanganate is added and the test sample is permitted to sit. A control sample of distilled water mixed with an equal amount of potassium permanganate is also prepared in a second container. After a period of time passes, the color of the test sample is compared to the color of the control sample. If the test sample is significantly lighter, additional potassium permanganate is added to the test sample and this procedure is repeated until the test sample achieves the color of the control solution. The amount of potassium permanganate needed to turn the test sample to the color of the control sample is directly proportional to the amount of organic material in the tank. If more than a specified amount is added, the level of organic material in the tank is too high and remedial measures are needed.

14 Claims, 1 Drawing Sheet

METHOD FOR MEASURING ORGANICS LEVELS IN AN AQUARIUM

BACKGROUND OF THE INVENTION

This invention relates generally to aquariums for tropical fish and more particularly to a method and apparatus for monitoring the level of organic material in the aquarium.

A typical fish tank 100 including a supply of water 110 is shown in FIG. 1. Organic material is introduced to water 110 of tank 100 from fish food, fish waste, decaying plant material, and other sources. Organic material is commonly removed from water 110 through the use of a filter 120 containing a layer of activated charcoal granules 125.

Filter 120 physically entraps the organic material within pores of charcoal granules 125. However, it is impractical for the typical hobbyist to determine whether charcoal 125 in filter 120 has lost sufficient activity to reduce organic material in aquarium water 110 to a suitable level. Consequently, hobbyists typically change the charcoal in their filters at periodic intervals or change the water.

Notwithstanding, there has been a need for the typical hobbyist to determine whether the water or charcoal should be changed more frequently, whether suitably active charcoal is being discarded prematurely, whether there are too many fish in the tank or whether the fish are being overfed.

There are various test kits available to the aquarium hobbyist for obtaining information about the condition of the water in a fish tank. Some kits provide information about the ammonia level, others measure nitrogen levels and still others determine the pH level of water in the tank. While knowing each of these conditions is important for maintaining the proper environment for fish in a tank, this alone is not satisfactory for maintaining a suitable environment for fish.

Accordingly, it is desirable to provide a method and apparatus for overcoming the deficiencies of the prior art.

SUMMARY OF THE INVENTION

Generally speaking, in accordance with the invention, a kit and method are provided for determining the water quality in an aquarium. A test sample of water is removed from an aquarium to a test sample container. The pH of the test sample cart be lowered and then a quantity of potassium permanganate is added and the test sample is permitted to sit, preferably for at least 30 minutes. A control sample of preferably an equal amount of distilled water mixed with an equal amount of potassium permanganate is also prepared in a second container. After a period of time passes, the color of the test sample is compared to the color of the control sample. If the test sample is significantly lighter, additional potassium permanganate is added to the test sample and this procedure is repeated until the test sample achieves the color of the control solution.

The amount of potassium permanganate needed to stabilize the test sample to the color of the control sample is directly proportional to the amount of organic material in the tank. If more than a specified amount is added, the level of organic material in the tank is too high and remedial measures are needed.

Accordingly, it is an object of the invention to provide aquarium hobbyists with a method and apparatus for improving conditions within their aquariums.

Another object of the invention is to provide a method and apparatus for determining whether it is necessary to change the charcoal in an aquarium filter.

A further object of the invention is to provide a method and apparatus for determining whether it is necessary to change the water or remove media such as resins in an aquarium.

Still another object of the invention is to provide a method and apparatus for determining whether fish in an aquarium are being overfed.

Still a further object of the invention is to provide a method and apparatus for determining whether the bioload in an aquarium is too high.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 2:
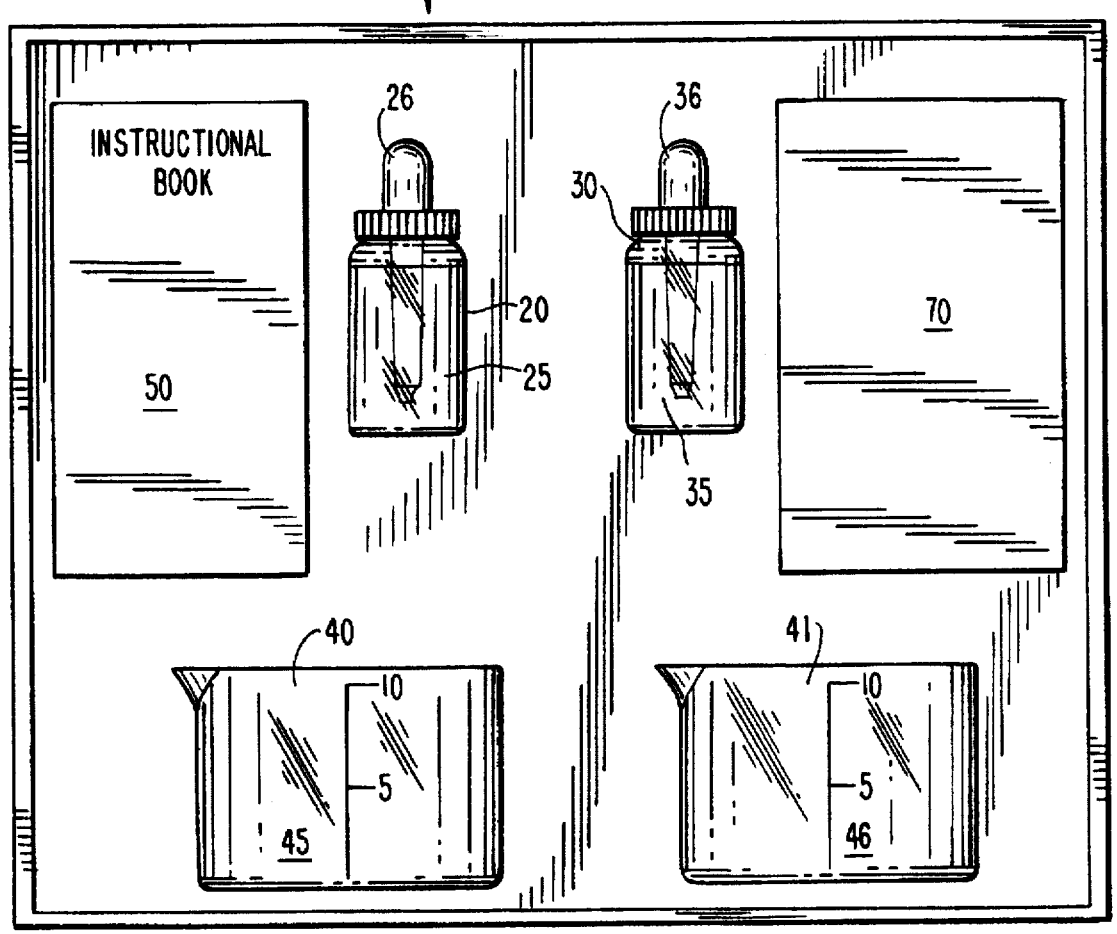
FIG. 2 is a perspective view of a kit for determining the level of organic material in a fish tank.
Figure 1:
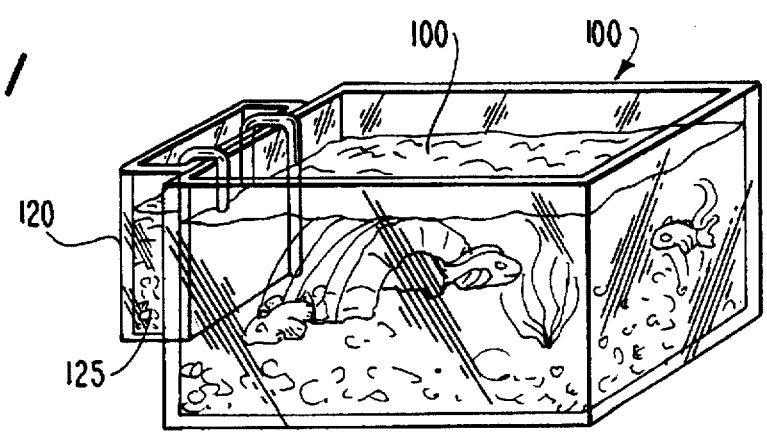
FIG. 1 is a perspective view of a typical fish tank.

It is desirable to maintain a healthy environment for fish in an aquarium. It has been determined that one way to achieve this goal is to monitor the level of organic material in the tank. Excess organic material in the tank has been determined to be unhealthy. For example, it can lead to stress on the fish population and can even cause their immune system to break down. Knowing this information can assist the typical aquarium hobbyist in determining when to discard charcoal or other organic removal media from the filter; change the water; whether there are too many fish in the tank; whether the fish are being overfed; and whether the fish are being unnecessarily stressed due to poor water quality.

To determine whether there is an acceptable level of organic material in a fish tank, a test sample of water is removed from the tank and placed in a container. The pH of this test sample is preferably reduced to an effective level to enhance the reaction and prevent precipitation of manganese oxide. Potassium permanganate ($KMnO_4$) is then added to the sample, which rams the sample pink. However, the potassium permanganate reacts with organics in the test sample and the sample becomes clear. By adding the potassium permanganate slowly, such as dropwise, and waiting to see if the color changes over time, the amount of organics in the test sample can be determined.

Next, a control sample of preferably an equal amount of distilled water is collected and preferably the same amount of potassium permanganate as was initially added to the test sample is added to the control sample. As soon as the test sample achieves the color of the control sample, there is an excess of potassium permanganate in the test sample and the relative amount of organics is known.

Typically, the organics from the aquarium water will react with the potassium permanganate and mm the test sample clear. If the pink color does not remain after a specified amount of time, such as 30 minutes, additional potassium permanganate is added to the test sample and the procedure is repeated until the color remains for 30 minutes. If more than a specified amount of the potassium permanganate is needed to maintain a pink color of the test sample, based on the size of the sample and strength of the permanganate added there is too much organic material in the aquarium water and a change is necessary.

Too much organic material in the aquarium is a signal that the carbon in the filter should be changed. After a few days, the water should be tested again by the above procedure. If the level of organics is still too high, the amount of food fed to the fish should be reduced. This might also be a sign that there are too many fish. If these are not causing the excessively high organic levels, it is possible that there is a dead fish or plant decaying in a hidden spot of the aquarium and should be searched for. Also, the water and other organic removal media can be changed.

A test kit and method in accordance with a preferred embodiment of the invention will be described more particularly with reference to FIG. 2. The specific volume amounts, chemicals and concentrations are provided for purposes of illustration only and the specific examples disclosed should not be interpreted in a limiting sense.

An organics test kit 10 constructed in accordance with a preferred embodiment of the invention is shown generally in FIG. 2. Test kit 10 includes a test sample beaker (vial) 40 and a control sample beaker 41. Beakers 40 and 41 preferably have a capacity of at least 10 ml and should include graduations of at least the 5 ml and 10 ml levels. Beakers 40 and 41 are preferably constructed from a clear corrosion resistent material such as glass.

Test kit 1 also includes a first dropper bottle 20 including potassium permanganate solution 25 which has a molar concentration of about 0.02%. A preferred range for potassium permanganate 25 is from about 0.01% to 0.10%. The 0.02% of permanganate solution 25 was chosen to balance the criteria of accurate results, perceivable color change and a suitable time frame. If the concentration of permanganate chosen is too high, it is difficult to control the amount added to the sample and either the volume of the test sample must be increased or the accuracy of the results will be reduced. If the concentration is too low, it will take too long to perform the test properly.

Bottle 20 is also provided with a dropper 26. It is constructed to provide drops having a volume of approximately 1/20 ml. The size of these drops is well suited for a test kit in which the test sample is 5 to 10 ml in volume and the concentration of potassium permanganate is about 0.01 to 0.10 percent. A 1/20 ml drop of 0.02% potassium permanganate solution 25 will have a concentration of 10 ppm (10 mg/liter) potassium permanganate.

Test kit 10 also includes an acid supply bottle 30 including a quantity of 30% by weight phosphoric acid 35. Phosphoric acid is preferred because it is relatively safe, to handle. Other acids could be used, such as weak solutions of hydrochloric acid or sulfuric acid. However, phosphoric acid in concentrations of 15 to 40 wt. %, preferably not more than about 30% is preferable in view of its relative safety.

The acid selected should be relatively safe to handle and should not interact with the potassium permanganate solution and lead to false readings. Thus, organic acids, such as carboxylic acid should not be used. The 30% concentration level is matched to the concentration of the potassium permanganate, the size of the drops and the size of the test sample. If the acid were stronger, there would be a loss in sensitivity. If the acid were weaker, it would have a diluting effect on the sample and could interfere with the accuracy of the results. It has also been found that adding acid leads to increased consistency in the organics/permanganate reaction.

Acid bottle 30 is also provided with a dropper 36. Dropper 36 is constructed to provide drops of approximately 1/20 ml in volume. This size is chosen to correlate to the size of the test sample and the concentrations of the various materials. Five drops are needed to reduce the pH of a 5 ml sample to an appropriate level of 1. The potassium permanganate reacts with organic material more quickly at low Ph. Furthermore, the acidity of the test sample will make more of the organics susceptible to reaction with potassium permanganate. Some organics will not react with potassium permanganate at high pH and the accuracy of the test can therefore be enhanced at lowered pH.

Test kit 10 can also include an instruction pamphlet 50 and a sheet of white paper 70. The instructions can also be provided on the side of a box or on a card. The instructions can be printed on a white card or the bottom of a box of kit 10 can also be made white.

To determine whether an aquarium has an unsuitably high level of organic material, a 5 ml test sample 45 from aquarium 100 is collected in sample beaker 40. A 5 ml control sample 46 of distilled water is placed in control beaker 41. The pH of test sample 45 is then reduced to about 1 by the addition of five drops of acid 35 from acid bottle 30. One drop of permanganate 25 from bottle 20 is added and the solution is mixed and set on white paper 70.

One drop of potassium permanganate solution 25 is also added to control sample 46 in control beaker 41. This should give the control solution a light pink color indicating an excess of permanganate. Control beaker 46 is then set next to sample beaker 40 on paper 70 and the beakers are permitted to sit for about 30 minutes so that the system in test beaker 45 can stabilize.

At that time, the color of test sample 45 is compared to the color of control sample 46. If test sample 45 is clear, or significantly lighter in color than control sample 46, this indicates that all of the potassium permanganate has been reacted with organics in the water and excess organics may exist. Therefore, an additional drop of potassium permanganate 25 is added to aquarium sample 45, mixed and permitted to sit for an additional 30 minutes. This procedure is repeated until aquarium sample 45 maintains a pink color at the end of the 30 minute period.

For typical aquarium situations, it is desirable that not more than three drops of potassium permanganate solution 25 are needed to maintain the pink color of test sample 45 at the end of the 30 minute period. If more than three drops are needed, this is an indication that the organics level in aquarium 100 is too high. This indicates that carbon 125 of filter 120 should be replaced. After a few days, the test should be repeated. If the organics level is still too high, there may be too many fish in the tank, too much food could have been added, the filters may not be running properly or there could be a dead plant or fish decaying in the tank. If five drops are needed, it is recommended that about half of the water in the aquarium should be replaced as the fish are likely to be under significant stress.

It will thus be seen that the objects set forth above, among those made apparent from the preceding description, are efficiently attained and, since certain changes may be made in carrying out the above method and the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method of determining the relative level of organic material in an aquarium, comprising the steps of:

removing a test sample of aquarium water having a first volume from an aquarium;

adding dropwise a predetermined mount of potassium permanganate to the aquarium water test sample from a potassium permanganate source; said predetermined amount of potassium permanganate corresponding to a predetermined number of drops from the potassium permanganate source;

permitting the color of the test sample to substantially stabilize and observing whether the substantially stabilized color of the test sample is pink, said pink color being substantially the color resulting when about the predetermined amount of potassium permanganate is added to distilled water of about the same volume as the volume of the test sample;

and determining that there is an excess level of organic material in the aquarium when the color of the substantially stabilized test sample is not substantially pink and that there is an acceptable level of organic material in the aquarium when the color of the substantially stabilized test sample is substantially pink.

2. The method of claim 1, wherein the pH of the test sample is lowered to a pH of about 1 by adding acid to the test sample prior to permitting the color of the test sample including the potassium permanganate to stabilize for the first time.

3. The method of claim 1, wherein the predetermined number of drops added to the test sample is one drop of potassium permanganate solution having a concentration from about 0.01% to 0.10%.

4. The method of claim 3, wherein the pH of the test sample is lowered to a pH of about 1 by adding acid to the test sample prior to permitting the color of the test sample including the potassium permanganate to stabilize for the first time.

5. The method of claim 1, wherein the potassium permanganate is provided in a kit including a written indication of the selected number of drops.

6. The method of claim 5, wherein the pH of the test sample is lowered to a pH of about 1 by adding acid to the test sample prior to permitting the color of the test sample including the potassium permanganate to stabilize for the first time.

7. The method of claim 1, wherein the potassium permanganate source is an aqueous solution having a concentration of from about 0.01% to 0.10%.

8. The method of claim 7, wherein the pH of the test sample is lowered to a pH of about 1 by adding an acid to the test sample, prior to permitting the color of the test sample including the potassium permanganate to stabilize for the first time.

9. The method of claim 8, wherein the acid is phosphoric acid, having a concentration from about 10% to 40% and the phosphoric acid is added dropwise to the test sample.

10. The method of claim 9, wherein the first volume of water is from about 5 to 10 ml.

11. The method of claim 9, wherein said pink color is indicated by preparing a control sample by adding the second amount of potassium permanganate to a sample of water of equal volume as the test sample, potassium permanganate is added drop wise to the test sample, the aquarium water test sample is permitted to stand for about 20 to 40 minutes to stabilize and an additional drop is only added if the aquarium sample solution is substantially lighter in color than the control sample.

12. The method of claim 9, wherein said pink color is indicated by preparing a control sample by adding the predetermined amount of potassium permanganate to a sample of water of equal volume as the test sample.

13. The method of claim 9, wherein the concentration of the potassium permanganate source, the strength of the acid, the volume of the test sample, the predetermined number of drops of potassium permanganate and the amount of acid added are adjusted so that an aquarium with an acceptable amount of organic material will be indicated by the predetermined number of drops amount of potassium permanganate being not more than about 5 drops added to the aquarium test sample.

14. The method of claim 13, wherein said pink color is indicated by preparing a control sample by adding the predetermined amount of potassium permanganate to a sample of water of equal volume as the test sample.

\* \* \* \* \*